(12) United States Patent      (10) Patent No.: US 8,557,095 B2
Troy et al.      (45) Date of Patent: Oct. 15, 2013

(54) ELECTRODE FOR WHOLE CELL AND OTHER TESTING

(75) Inventors: John B. Troy, Evanston, IL (US); Samsoon Inayat, Evanston, IL (US); Donald R. Cantrell, Evanston, IL (US); Yan Zhao, Chicago, IL (US); Dmitriy A. Dikin, Skokie, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/135,393

(22) Filed: Jul. 1, 2011

(65) Prior Publication Data

US 2012/0006694 A1     Jan. 12, 2012

Related U.S. Application Data

(60) Provisional application No. 61/399,078, filed on Jul. 7, 2010.

(51) Int. Cl.
*G01N 27/403* (2006.01)
*G01N 27/327* (2006.01)

(52) U.S. Cl.
USPC .... 204/400; 204/403.01; 205/792; 435/286.1

(58) Field of Classification Search
USPC ........... 205/775, 792; 204/400; 435/461, 470, 435/173.6, 285.2; 73/864.01–864.24
See application file for complete search history.

(56) References Cited

PUBLICATIONS

Lollike et al., J. Cell. Biol. 129, 99-104.*

E. Neher et al., "Single-channel currents recorded from membrane of denervated frog muscle fibres", Nature, vol. 260, pp. 799802, Apr. 1976.
O.P. Hamill et al., "Improved Patch Clamp Technique for high-resolution current recording from cells and cell-free membrane patches", Pflugers Archive European J. of Physiology, vol. 391, pp. 85-100, Aug. 1981.
H. Sontheimer et al., "Whole-Cell Patch Clamp Recordings", Patch Clamp Analysis: Advanced Techniques, 2nd Ed., Neuromethods, 38, pp. 35-68, 2007.
"Instrumentation for measuring Bioelectric signals from cells", The Axon Guide, 2nd Ed., Molecular Devices, USA. pp. 59.
A.J. Sherman et al., "Series resistance compensation for whole-cell patch-clamp studies using a membrane state estimator", Biophysical J., vol. 77, pp. 2590-2601, Nov. 1999.
S.F. Traynelis, "Software-based correction of single compartment series resistance errors", J. of Neuroscience Methods, vol. 86, pp. 25-34, 1998.
F. Bensanilla et al., "Gating Currents", Methods in Enzymology, vol. 293, pp. 331-352, 1998.
J.T.Davie et al., "Dendritic patch clamp recording", Nature Protocols, vol. I, No. 3, pp. 1235-1247, Nov. 2006.
A. Marty et al., "Diffusion into the patch-clamp recording pipette of a factor necessary for muscarinic current response", Cell Signal vol. I, No. 3, pp. 259-268, 1989.
W. Walz, "Perforated Patch-Clamp Technique", Patch-Clamp Applications and Protocols, Neuromethods, 26, 155-171, 1995.

(Continued)

*Primary Examiner* — Luan Van
*Assistant Examiner* — Steven Rosenwald

(57) ABSTRACT

A pushpen electrode is provided for electrophysiology measurements. The pushpen operation is used to impale a cell membrane in cell-attached configuration to go whole-cell without disruption of the gigaseal. The pushpen electrode has advantages over the conventional patch clamp electrode in reducing tip series resistance, increasing signal bandwidth, permitting longer-term recordings and reducing diffusion between the cytosol and the electrode solution.

7 Claims, 8 Drawing Sheets

(56) References Cited

PUBLICATIONS

Y. Zhao et al., "Patch clamp technique: review of the current state of the art and potential contributions from nanoengineering" J. of Nanoengineering and Nanosystems, vol. 222, pp. 1-11, 2009.

G. Miesenbock et al., "Visualizing secretion and synaptic transmission with pH-sensitive green fluorescent proteins," Nature, vol. 394(6689), pp. 192-195, 1998.

G. Dernick, "Simultaneous detection of Fusion and secretion by patch amperometry of exocytosis of small vesicles", PhD Dissertaion Carola University of Heidelberg, Germany, 1999.

H. Nadeau et al., "Two-compartment model for whole-cell data analysis and transient compensation", Journal of Neuroscience Methods, vol. 99, pp. 25-35, Mar. 2000.

X.M. Shao et al., "Micro-agar salt bridge in patch-clamp electrode holder stabilizes electrode potentials", Journal of Neuroscience Methods, vol. 159, pp. 108-115, Jul. 2007.

pClamp 10, "Data Acquisition and Analysis for Comprehensive Electrophysiology", User Guide, Molecular Devices, USA, pp. 163-166.

M. Sokabe et al., "The structure and dynamics of patchclamped membranes: a study of differential interference microscopy", J. of Cell Biology, vol. I 11, pp. 599-606, 1990.

T.M. Sushyna et al., "Biophysics and Structure of the Patch and the Gigaseal", Biophysical J., vol. 97, pp. 738-747, Aug. 2009.

L.H. Pinto et al., "Influenza virus M2 protein has ion channel activity", Cell, vol. 69, pp. 517-528, 1992.

V. Balannik et al., "Solid supported membrane technology for the investigation of the influenza A virus M2 Channel Activity", Pflugers Archive European J. of Physiology, vol. 459(4), pp. 593-605, Nov. 2009.

C. Wang et al., "Ion Channel activity of influenza A virus M2 protein: characterization of the amantadine block", JJ of Firology, vol. 67, pp. 5585-5594.

I.V. Chizhmakov et al., "Selective proton permeability and pH regulation of the influenza virus M2 channel expressed in mouse erythroleukaemia cell", J. of Physiology-, vol. 494 (2), pp. 329-336, Jul. 1996.

Y. Zhao et al., "Impedance characterization and modelling of an improved patch clamp device", J. of Nanoengineering and Nanosystems, 2009, 223, pp. 121-131.

I.V. Chizhmakov et al., "Differences in conductance of M2 proton channels of two influenza viruses at low and high pH", JJ of Physiolop., vol. 546 (2), pp. 427-438, Jan. 2003.

K. Giffin et al., "Novel assay for the influenza virus M2 channel activity", Federation of European Biochemical Societies. Letters, vol. 357, pp. 269-274, 1995.

G. Dernick et al., "Patch amperometry: high resolution measurements of single-vesicle fusion and release", Nature Methods, vol. 2(9), pp. 699-708, Sep. 2005.

\* cited by examiner

Wire tip back

Wire tip protruding (a) Pushpen operation with Ag/AgCl wire with an Ag tip

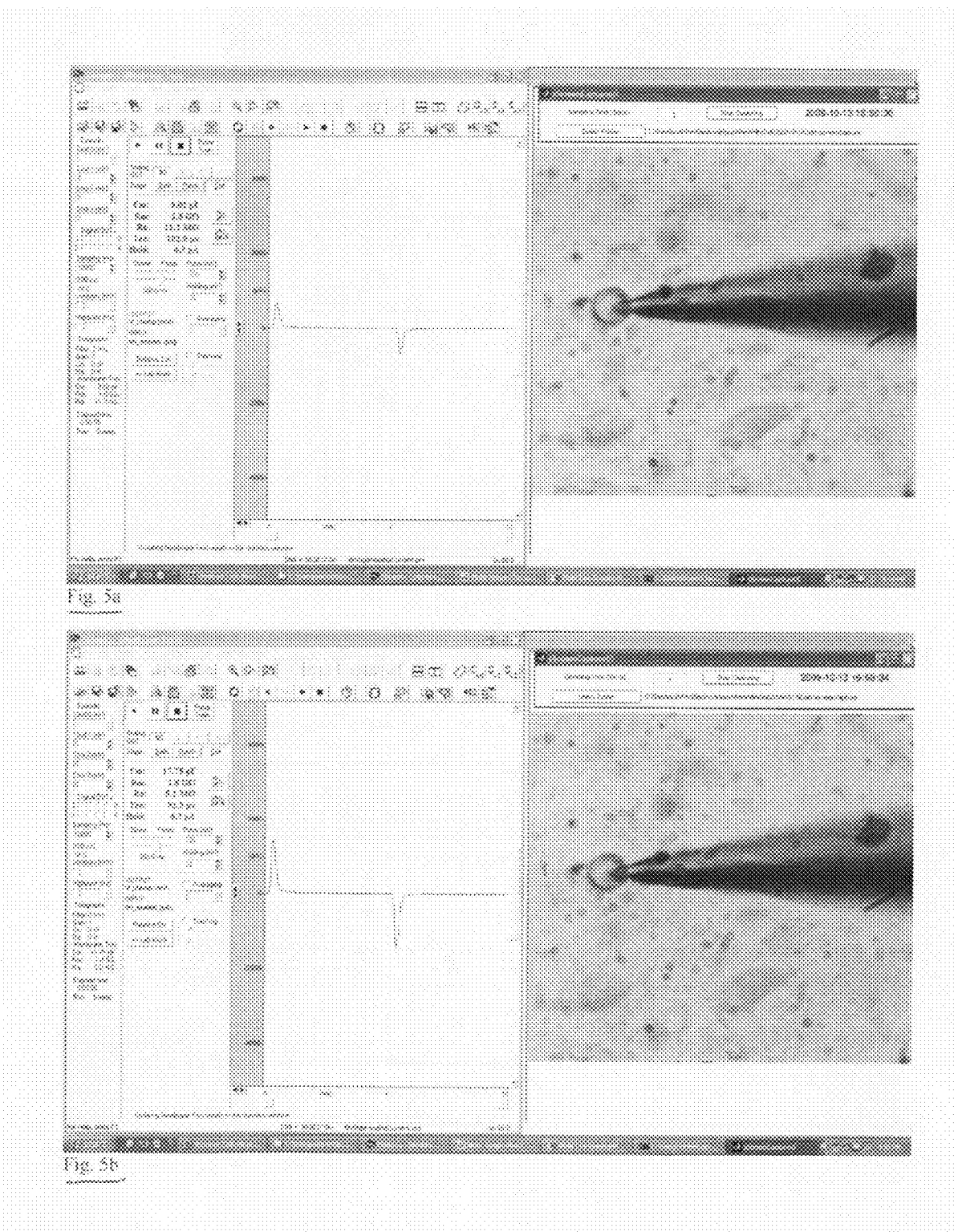

ELECTRODE FOR WHOLE CELL AND OTHER TESTING

This application claims benefits and priority of U.S. provisional application Ser. No. 61/399,078 filed Jul. 7, 2010, the entire disclosure of which is incorporated herein by reference.

CONTRACTUAL ORIGIN OF THE INVENTION

This invention was made with government support under Grant No. DBI-0551852 awarded by the National Science Foundation. The government has certain rights in the invention.

BACKGROUND OF THE INVENTION

The patch clamp technique [references 1, 2] is the gold standard in neuroscience, cell biology, and pharmacology to study the electrophysiological properties of membrane-embedded proteins that regulate the ionic permeability of the plasma membrane-ion channels, receptors, and transporters. Changes in membrane-permeability result in ionic membrane currents and respective changes in transmembrane voltage. "Patch clamp" refers to recording these electrical signals from a membrane-patch (or entire membrane in whole-cell) using electronic circuitry which clamps either the membrane current or the transmembrane voltage to a desired value or a desired time course. In combination with patch-clamping, investigators also apply and record other signals such as chemical, mechanical, thermal, magnetic, and electromagnetic waves. The analysis of recorded stimulus-response data sets allows one to infer the roles of membrane-embedded proteins in the macro and microscopic phenomena involved in intra- or intercellular communication.

In a conventional whole-cell patch-clamp experiment, a pipette containing an electrolyte solution is used to gain electrical access to the interior of the cell (FIG. 1). A stationary Ag/AgCl wire in the pipette contacts the solution and connects to the amplifier input. The pipette is advanced towards the cell until its tip touches the plasma membrane. Gentle suction then applied inside the pipette seals its tip with the cell membrane. The seal is called a "Gigaohm seal" or a "Gigaseal" as its electrical resistance must exceed several G$\Omega$ to allow reliable recordings. The pipette-cell configuration in this instance is called "cell-attached". In order to obtain whole-cell configuration, a somewhat larger amount of suction is applied inside the pipette than was required for forming the seal, thereby rupturing the cell membrane giving the amplifier "low" (k$\Omega$ ohms or M$\Omega$) resistance electrical access to the interior of the cell. In an alternative, less common, method of achieving the whole-cell configuration, a voltage pulse usually called "zap" is applied to breakdown the lipid bilayer, though this technique does not always work for all cell types.

Although widely used, the conventional whole-cell patch-clamp experiment is laborious and has a low yield owing to the following problems.

1. It is difficult to form and maintain gigaseals and obtain whole-cell configuration from cell-attached mode. The experimenter has to practice and gain experience in order to do so. In case of a failure to obtain whole-cell configuration with one pipette, the experimenter has to replace it with a new one. Even experienced experimenters often have to try a couple of pipettes before they achieve whole-cell configuration. Currently, there are no alternative methods other than those mentioned above to obtain whole-cell configuration in patch clamp experiments.

2. The presence of series (or access) resistance results in voltage clamp errors and limits the bandwidth of the recorded signals. The bulk of series resistance is located at the pipette tip, the narrowest region of the conduction channel. This resistance sometimes increases during an experiment when cellular components migrate to and reduce the conduction channel [3]. To counter these problems, patch clamp amplifiers and data analysis software provide ways to compensate for series resistance [4], [5], [6]. However, compensation can be inadequate while recording high frequency signals (such as gating currents) [7] or while recording from small neural structures [8] such as dendrites or axons.

3. In some experiments, the diffusion of cytosolic chemicals into the pipette or components of the pipette solution into the cytosol, can dilute soluble components of the cytoplasm needed for ion channel function thereby resulting in erroneous results [9]. One approach to overcoming this problem is to reduce the pipette orifice diameter limiting diffusion but at the cost of an increase in series resistance. When this approach is not viable, cytosolic extract can be added to the pipette solution to minimize ionic concentration gradients reducing diffusion. The "perforated patch configuration" is an alternative from cell-attached mode where the membrane perforation is attained with ionophores (e.g. ATP, polyene antibiotics) [10]. The later two methods are laborious and difficult to carry out.

The conventional patch clamp technique has resulted in a large number of productive studies. However, there remains room to improve the patch clamp electrode to provide a coherent solution to the problems mentioned above.

SUMMARY OF THE INVENTION

The present invention accomplishes this by providing an electrode for electrophysiology measurements with push-pen operation using a motorized pipette holder. In the push-pen operation, a wire with a cell membrane-impaling tip moves linearly within a pipette such that its tip can protrude from the pipette tip like a push-pen. The push-pen method of operation is intended to be used advantageously to impale the cell membrane to obtain whole-cell configuration from a cell attached state, to clear clogged pipette tips, to reduce series resistance and to prevent cytosol diffusion into the pipette by physically obstructing the opening in the cell membrane, all without disrupting the gigaseal or applying a pulse of suction.

To this end, the present invention provides an electrode comprising a pipette having an open tip, an electrical or electrochemical transducer movably disposed in the pipette, and an actuator that operates to move the transducer toward the pipette open tip.

In one embodiment of the invention, the tranducer includes a pointed end movable past and outside of the pipette open tip. In an illustrative embodiment of the invention, the transducer is a silver wire coated with AgCl and having a pointed wire end that is movable past the pipette open tip.

In another embodiment of the invention, the electrode includes a protrudable member movable in the pipette by an actuator and on which protrudable member the transducer is disposed and insulated wherein the transducer moves with the protrudable member in the pipette and wherein the protrudable member has a pointed end movable past and outside of the pipette open tip. The protrudable member can comprise a point tipped metallic rod or point tipped metallic tube. In an illustrative embodiment, the transducer is a silver wire coated with AgCl wound on an insulating tube disposed around the protrudable member.

In practicing the invention, the actuator can comprise a hydraulic actuator, an electrical actuator, or other suitable actuator.

A method embodiment envisions using the electrode for electrophysiology testing, such as whole-cell patch clamping, or using one or two of the patch clamp electrodes for two-electrode voltage clamping. Other method embodiments envision using the electrode to test liposomes and artificial lipid bilayers, ion channels of cells as well as other tests.

Other advantages of the present invention will become more apparent from the following detailed description taken with the following drawings.

BRIEF DESCRIPTION OF THE DRAWINGS

FIG. 1a is a schematic diagram of a conventional pipette holder, while

FIG. 2a is a schematic diagram of an electrode with a motorized push-pen pipette holder pursuant to the invention, while

FIG. 3a is a schematic view of an electrode with a motorized push-pen pipette holder pursuant to the invention based on hydraulic actuator, while

FIG. 5a is a screen image (Clampex and Motic Image Plus windows) of a cell-attached configuration wherein the tungsten wire tip has not yet impaled the cell membrane, while FIG. 5b is a screen image of a whole-cell configuration after the tungsten wire tip has impaled the cell membrane by advancing the wire tip by a 200 nm step forward relative to the position shown in FIG. 5a.

DETAILED DESCRIPTION OF THE INVENTION

The present invention provides an electrode for electrophysiology measurements comprising a motorized pipette holder to provide a push-pen operation wherein a wire with a cell-membrane impaling tip moves linearly within the pipette such that its tip can protrude from the pipette tip like a push-pen. The push-pen method of operation is intended to be used to impale the cell membrane to obtain whole-cell configuration from a cell attached state, to clear clogged pipette tips, to reduce series resistance and to prevent cytosol diffusion into the pipette by physically obstructing the opening in the cell membrane, all without disrupting the gigaseal or applying a pulse of suction.

Figure 2A:
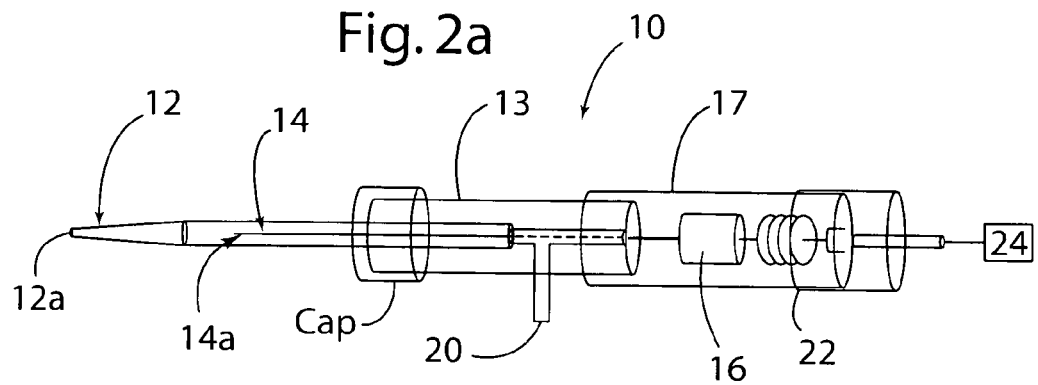
Figure 2B:
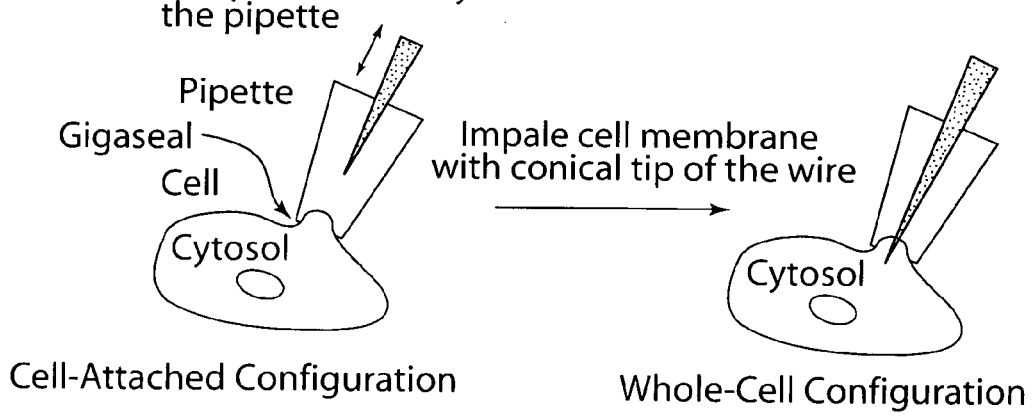
FIG. 2b illustrates schematically the push-pen operation to go whole-cell.

Referring to FIG. 2a, an initial embodiment of the present invention provides an electrode 10 comprising a pipette 12 having an open tip 12a, an electrical or electrochemical transducer 14 movably disposed in the pipette, and an actuator 16 that operates to move the transducer toward the pipette open tip. The transducer 14 includes a pointed end 14a movable past and outside of the pipette open tip 12a. For purposes of illustration and not limitation, the transducer 14 is a silver wire coated with AgCl and having a pointed wire end 14a that is movable past the pipette open tip 12a and the actuator 16 comprises a linear electrical or other motor in actuator housing 17. The pipette 12 is received in a capped cylindrical body 13. A suction tube or passage 20 is provided in the body and communicates with the interior of the pipette 12 as illustrated for drawing a relative vacuum therein. The transducer wire is connected to an electrical adapter fitting 22 that fits to a headstage of an amplifier 24, such as an Axopatch 200A Headstage available from Molecular Devices, Inc. Sunnyvale, Calif.

Figure 1A:
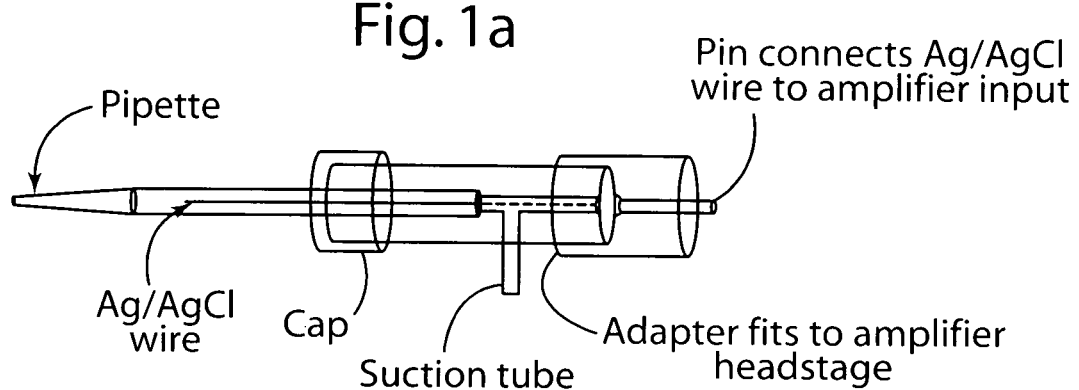
Figure 1B:
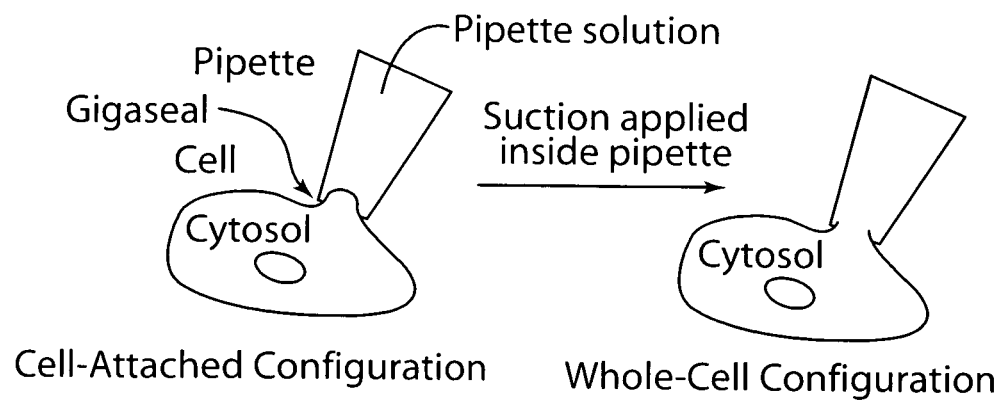
FIG. 1b illustrates schematically the conventional procedure for whole-cell testing.
Figure 3A:
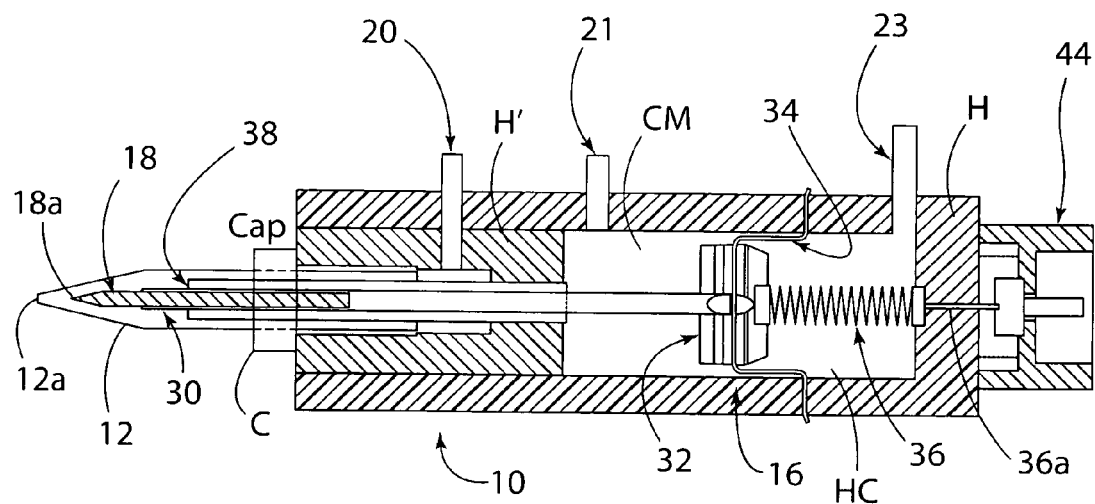
Figure 3B:
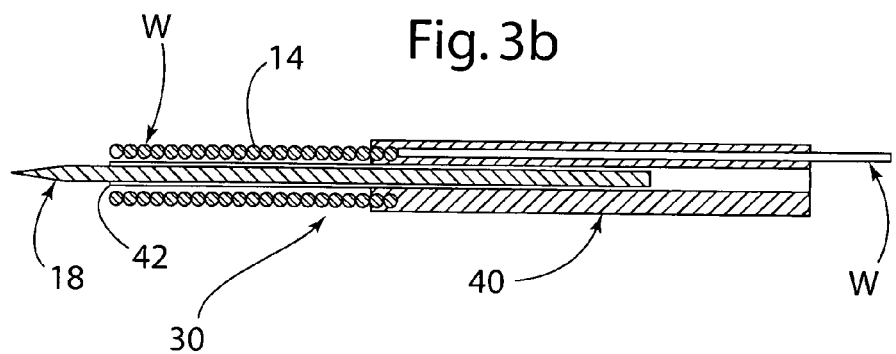
FIG. 3b is a schematic view of a carrier assembly that attaches to and moves with a cylinder fitted inside a diaphragm.
Figure 3C:
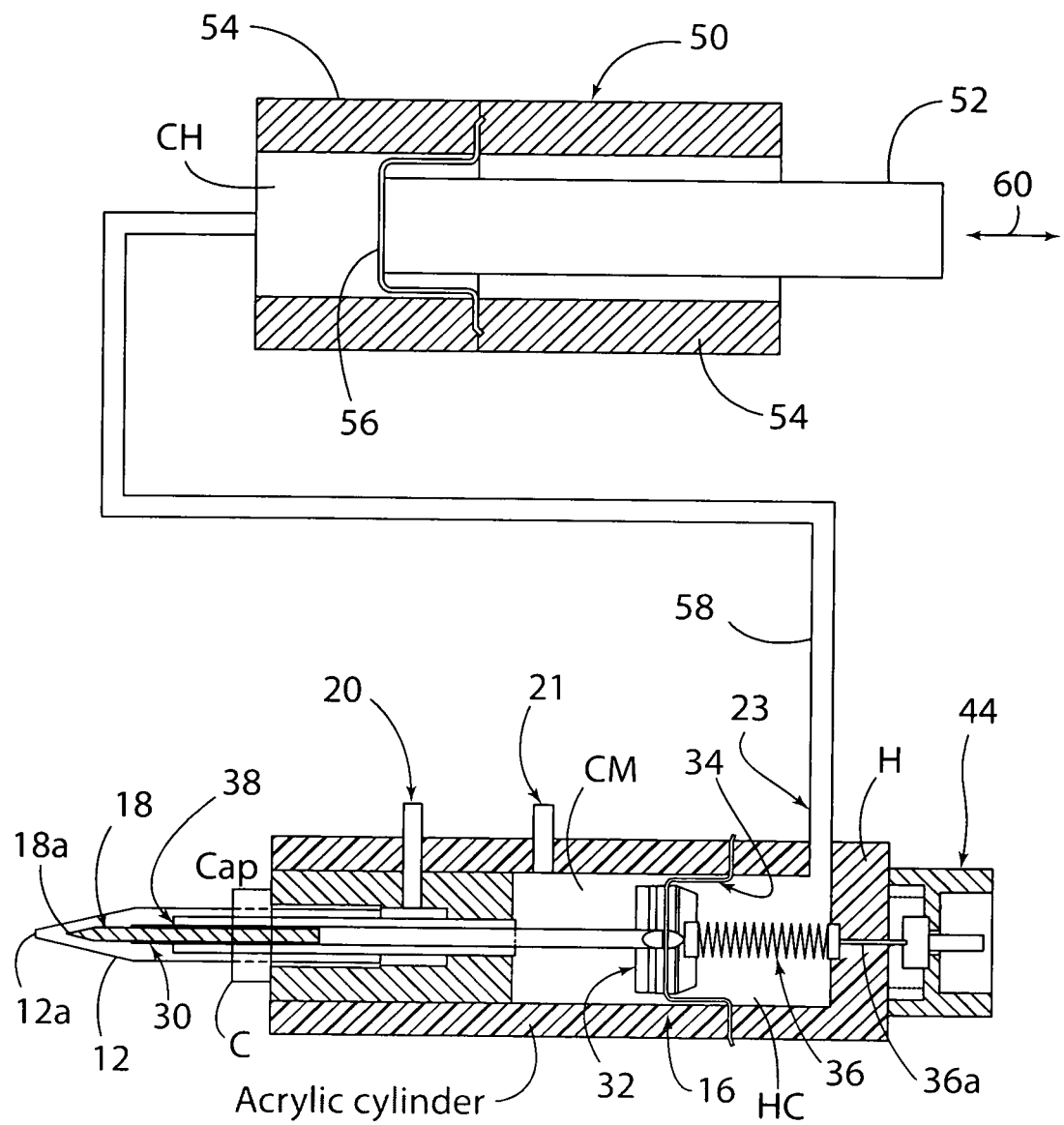
FIG. 3c is a schematic view of the push-pen pipette and the hydraulic actuator.

For comparison, FIGS. 1a, 1b, and 1c show an electrode with a conventional pipette holder and method to effect whole-cell operation Referring to FIGS. 3a, 3b, and 3c, another illustrative embodiment of the invention provides an electrode 10 that includes a pipette 12 and an electrical or electrochemical transducer 14 disposed on a protrudable member 18 residing on a carrier assembly 30 that is movable in the pipette 12. The carrier assembly 30 is movable by actuator 16 and carries the protrudable member 18 and the transducer 14. The protrudable member 18 has a pointed end 18a movable past and outside of the pipette open tip 12a. The protrudable member 18 can comprise a point tipped metallic rod or point tipped metallic tube. The metallic rod or tube can be tungsten or other metal or alloy for purposes of illustration and not limitation. The actuator 16 can comprise a hydraulic actuator as illustrated in FIGS. 3a and 3c, an electrical actuator, or other suitable actuator.

The housing H includes a fixed housing insert H' having a counter bore in which the pipette is received and held by an o-ring tightened onto the pipette by a threaded cap C on the housing insert H'. The housing and housing insert include a suction tube and passage 20 that communicates with the interior of the pipette 12 for drawing a relative vacuum therein. The housing H can comprise an acrylic cylinder for purposes of illustration and not limitation. The housing insert likewise is made of acrylic.

For purposes of illustration and not limitation, the carrier assembly 30 shown in FIG. 3b resides and is movable in an outer protector tube 38 (e.g. AWG 23 polyimide tube shown in FIG. 3a) on which the pipette 12 is loaded and held by an o-ring tightened onto the pipette by threaded cap C on the housing insert H'. The carrier assembly 30 attaches to and moves with metal (e.g. aluminum) or other cylinder 32 fitted to a rubber or other diaphragm 34 of the hydraulic actuator 16. An extension spring 36 and associated pin 36a are disposed between the diaphragm and housing H of the electrode. The perimeter of the diaphragm 34 is anchored to the housing H as shown. The housing H can comprise an acrylic cylinder for purposes of illustration and not limitation.

The carrier assembly 30 is shown comprising an outer tubular sleeve 40 (e.g. AWG 26 polyimide tube) that can slide back and forth in the fixed outer protector tube 38 and is connected to the diaphragm 34 by the aluminum cylinder 32 so as to move in response to movement of the diaphragm 34.

The protrudable member 18 fits snuggly in the inner holder tube 42 which is glued inside the outer tubular sleeve 40 so as to slide back and forth therewith in the protector tube 38.

The transducer 14 is electrically insulated from the protrudable member 18. In an illustrative embodiment of the invention, the transducer 14 is a silver wire W coated with AgCl and wound on an insulating inner holder tube 42 (e.g. AWG 34 polyimide tube), FIG. 3b. The protrudable member 18, inner holder tube 42, and transducer 14 thus move as a unit. For purposes of illustration and not limitation, a 50 μm diameter Ag/AgCl coated wire W is wound on the exterior of the electrical insulating, inner holder tube 42 and is directly connected to the metal (aluminum) cylinder 32. The transducer 14 is electrically insulated from the protrudable member 18 by the inner holder tube 42. The aluminum cylinder 32 is connected to an electrical adapter fitting 44 by an extension spring 36 and spring pin 36a. The adapter fitting 44 fits to a headstage of an amplifier (e.g. amplifier 24 of FIG. 2a), such as an Axopatch 200A Headstage available from Molecular Devices, Inc, Sunnvale, Calif.

The hydraulic diaphragm 34 is actuated by a hydraulic driver 50, FIG. 3c, that comprises an aluminum rod 52 driven to and fro by a linear micropositioner motor (actuator) 60 to vary hydraulic fluid pressure (light mineral oil in driver cylinder 54). The rod 52 resides in the driver cylinder 54 (e.g. acrylic cylinder) and actuates a rubber or other diaphragm 56 therein to vary hydraulic pressure in the hydraulic chamber HC formed between the diaphragm 34 and the housing H to move the carrier assembly 30 and thus the components thereon. Hydraulic conduit 58 connects the hydraulic chamber CH of driver cylinder 54 and the hydraulic chamber HC via housing tube and/or passage 23. The housing H also includes a tube and/or passage 21 to introduce light mineral oil (hydraulic fluid) into the chamber CM in front of the diaphragm 34 to help obtain gigasealing.

The present invention envisions using the electrode as a patch clamp electrode for electrophysiology testing, such as whole-cell patch clamping, or using one or two of the patch clamp electrodes for two-electrode voltage clamping. Other method embodiments envision using the electrode to test liposomes and artificial lipid bilayers, as well as other tests.

The following Examples are offered to illustrate, but not limit, the invention.

EXAMPLES

Materials and Methods

A. Motorized Pipette Holder

FIGS. 3a, 3b, and 3c show schematic views of the electrode with the motorized pipette holder based on a hydraulic actuator. The bodies of the pipette holder and driving hydraulic cylinder were machined from an acrylic rod (catalog # ZCAR-24-12, Small Parts, Inc. FL, USA). The hydraulic diaphragms (34, 56) used in both the driver and driven hydraulic cylinders were acquired from David Kopf Instruments, CA, USA (catalog #607-07). Light mineral oil (catalog #330779, Sigma-Aldrich, MO, USA) is used as the hydraulic fluid. The diaphragm (56) of the driver cylinder is moved by a linear actuator and controller David Kopf Hydraulic Micropositioner 650 (David Kopf) as shown in FIG. 3c having a motion resolution of 200 nm/step. The aluminum cylinder (32) is incorporated in the diaphragm of the driven cylinder, which is attached to the amplifier input via the connector pin and an extension spring shown (catalog # ESX-0004-10, Small Parts). In the same metal cylinder, the carrier assembly (FIG. 3b) assembled from 50 μm diameter silver wire (catalog #44461, Alfa Aesar, MA, USA), and triple-wall polyimide tubing (AWG 34, 26, Small Parts). The silver wire was coated with AgCl by placing it in a 3M KCl solution and passing dc electrical current through it. The outer protector tube (38) is AWG 23, from Small Parts. The carrier assembly, FIG. 3b, attaches to and moves with the aluminum cylinder (32) fitted inside the diaphragm.

The travel of the actuator (60) was about 20 mm with a resolution of 200 nm/step. The introduction of mineral oil on the left side of the diaphragm, FIGS. 3a, 3c, is used to help obtain gigaseals. FIG. 3b is a schematic of the carrier assembly that contains the tungsten and Ag/AgCl wires as an electrical or electrochemical transducer to transduce a voltage or ionic current in the patch clamp testing. The tungsten wire (18) is snug fit into the polyimide holder tube (42). To change pipettes, the tungsten wire (18) is retracted back into the protector tube (38).

B. Inner Wire with Conical Tip

The protrudable tungsten wire (18) with conical tip (18a) is an etched tungsten wire acquired from Advanced Probing Systems, Inc. CO, USA (catalog # WAP5-150-01x2.0). The tungsten wire diameter is 127 μm, the conical tip diameter is <<500 nm and cone length is between 5 and 6 mm.

C. Pipette Fabrication

Pipettes were pulled on a Sutter P-87 Glass Puller from Corning 8161 Patch Glass (OD 1.5 mm, ID 1.1 mm, and 10 cm length) with the following program; Heat 500, Pull 0, Vel 40, Time 250. The puller was equipped with a box type filament. A typical glass pipette had an overall length of 5 cm, a cone length of about 4 mm and an open tip orifice diameter of about 1-2 μm.

D. CHO-KI Cell Culture and Transfections

CHO-KI cells (Clontech, Mountain View, Calif.) were cultured at 37° C. (humidified atmosphere 5% $CO_2$), on 25 $cm^2$ culture flasks (BD Bioscience, San Jose, Calif.) in F12-Kaighn's modification medium (Hyclone, Logan Utah) containing 10% Fetal Bovine Serum (Sigma) and 1% penicillin/streptomycin (Invitrogen, Carlsbad, Calif.). Once the cell culture was about 90% confluent in a flask, it was split at a ratio of 1:10 by detaching with trypsin (Sigma) and EDTA (Invitrogen). For transfection and patch-clamp electrophysiology, the cells were subcultured on coverslips in a 35 mm petri dish (Falcon). Sixteen to twenty-four (16-24) hours before patch-clamp experiments, the cells were transfected with plasmid cDNA of Influenza A virus protein A/M2 and a fluorescent protein pHluorin [12]. Lipofectamine 2000 reagent (Invitrogen) was used to transfect with a total plasmid cDNA of 5 μg per petri dish.

E. Whole-Cell Patch-Clamp Measurements

Patch-clamp experiments on non-transfected and transfected CHO-K1 cells (expressing A/M2 and pHluorin proteins) were performed with a conventional pipette holder (described previously in [20]), and using the motorized pipette holder of FIGS. 3a-3c pursuant to the invention to obtain whole-cell configuration in a novel way. The coverslip with CHO-K1 cells was broken into small pieces in the petri dish and one piece placed in a chamber on an inverted microscope (Olympus IMT2) to perform electrophysiology. The chamber was perfused with a solution of the following composition (concentrations in mM); NMDG (135), HEPES (25), $CaCl_2$ (5), glucose (10), pH 7.4 adjusted with methanesulfonic acid. This solution is non-activating for the A/M2 protein channel. The activating solution contained the following in mM; N-Methyl-D-Glucamine (NMDG) (135), MES (25), $CaCl_2$ (5), glucose (10), pH 6.0 adjusted with methanesulfonic acid. To inhibit the A/M2 channel, non-activating solution containing 100 μM amantadine was applied for 1 minute. Transfected cells were identified by fluorescence in response to a 450 nm wavelength light (excitation wavelength for pHluorin).

All whole-cell measurements were performed at room temperature (22-24° C.) with a holding potential of 0 mV using an Axopatch 200A amplifier (Molecular Devices, CA, USA). The low-pass filter on the amplifier for current signals was set to give a cut-off of 2 kHz. Digitization was performed using Digidata 1440A (Molecular Devices) at 10 kHz and the current signal was recorded with Clampex 10.2 (Molecular Devices). The signals were plotted using Matlab R2008a (The Mathworks, Inc). In all experiments, the pipette resistance was 5-10 MO with a solution of the following composition (concentrations in mM); NMDG (135), HEPES (25), and EGTA (5), pH 7.2 adjusted with methanesulfonic acid. The series resistance did not exceed 15 MΩ (as reported by the Clampex 10.2 software [16]). No series-resistance compensation was applied. The A/M2 proton channel is a low conductance ion channel with maximum currents of less than 100 pA in our preparations and thus the maximum series resistance error would be less than 1.5 mV.

F. Imaging

A 1.3 MPixels, USB 2.0, camera Moticam 1000 (Motic, Xiamen, China) with Motic Image Plus 2.0 image acquistion software was used. The camera was mounted on the eyepiece of the microscope. Additionally, a custom matlab script was written to capture whole screen images at a sampling interval of 3 seconds in order to obtain Clampex membrane-test waveforms and Motic images simultaneously.

III. Results and Discussion

A. Pushpen Patch Clamp Electrode

Figure 4A:
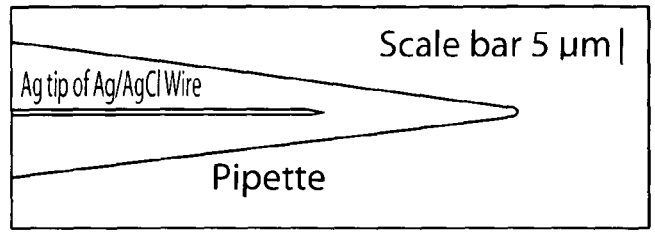
FIGS. 4a and 4b are images, taken by an optical microscope, of the pipette push-pen operation with an Ag/AgCl wire with a Ag tip showing the wire tip back in FIG. 4a and protruding in FIG. 4b, respectively.
Figure 4B:
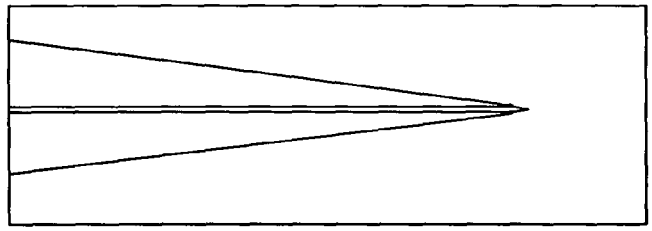
Figure 4C:
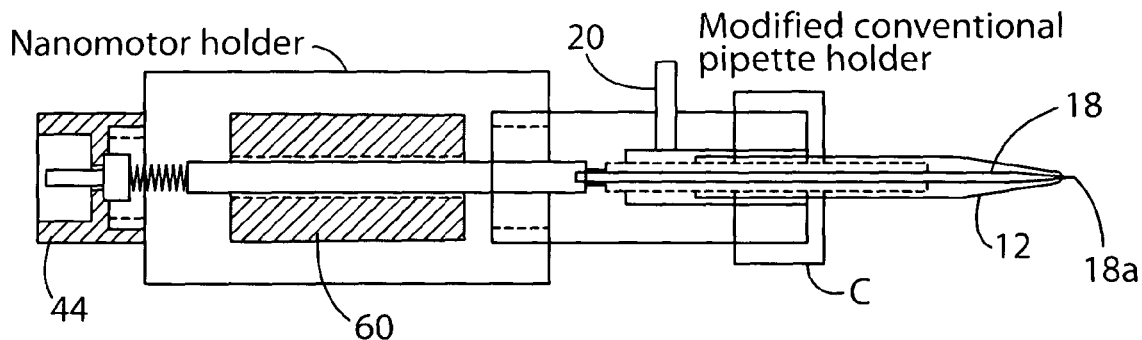
FIG. 4c is a schematic diagram of the piezoelectric actuator (Klocke nanomotor) based motorized pipette holder.

The design and development of the novel "Pushpen patch clamp electrode" for whole-cell patch clamp experiments involved two major steps, 1) achieving Pushpen operation with a matched pipette 12 and conical-tipped wire 18, and 2) developing a motorized pipette holder. Referring to FIGS. 4a, 4b, 4c, to initially implement the Pushpen operation, applicants started with pipette 12 and etched silver (Ag) wire 18, making the cone angle of the wire tip 18a less than that of the pipette. The initial design dimensions for the pipette tip diameter were set at 1-2 µm, appropriate for whole-cell patch clamping with mammalian cells. Each etched Ag wire was coated with AgCl and the Pushpen operation was achieved using a piezoelectric linear actuator for the required pipette dimensions (FIG. 4c). However, since Ag is a soft metal and the etched tips proved fragile, a tungsten wire was used with a conical tip coated or wound with Ag/AgCl to test the Pushpen operation for whole-cell patch clamp experiments.

To build a motorized pipette holder, a piezoelectric linear actuator 60 comprising a nanomotor from Klocke, Nanotechnik, Germany was used, having a resolution of 20 nm/step. FIG. 4c shows the schematic of the electrode using this piezoelectric actuator-based pipette holder. Although, the first successful Pushpen operation (FIGS. 4a and 4b) was implemented, due to design, electrical noise when tested with an Axopatch 200A amplifier, availability, and cost related issues with the piezo-nanomotor, applicants developed the electrode having the motorized pipette holder with a hydraulic actuator as shown in FIGS. 3a, 3b, 3c and described above to test the feasibility of the Pushpen operation with cells. Compared to the piezoelectric actuator, the hydraulic actuator has poorer motion resolution but much lower electrical noise and is inexpensive. The description below describes the characteristics of the motorized electrode using the hydraulic actuator, FIGS. 3a, 3b, and 3c.

Travel, Resolution and Backward Drift:

The total travel of the driven diaphragm (34) of the electrode of FIGS. 3a, 3b, 3c is about 20 mm. This ensures that enough of the 50 µm Ag/AgCl wire remains immersed in the pipette solution for effective conduction (without large offset potentials). The motion resolution of our actuator (60) is 200 nm/step, which is good enough to obtain whole-cell configuration with the Pushpen operation. The backward drift of the electrode due to leakage in the hydraulic assembly is about 1 µm over 5 minutes. Although this drift is insignificant for attaining whole-cell configuration and maintaining longer duration whole-cell recordings, drift can be reduced in other whole-cell experiments (e.g., preventing cytosolic diffusion into the pipette).

Electrical Noise:

Initially, applicants used double distilled water (resistivity 18 MOhm-cm at 25° C.) as hydraulic fluid, but the body of water surrounding the conduction pathway [metal cylinder in the diaphragm (34) and extension spring (36)] induced a large amplitude noise (>50 pA peak to peak). Thus, applicants redesigned the hydraulics to incorporate the use of light mineral oil. In order to reduce the electrical noise further, the electrode was shielded with aluminum foil. The presence of this shield increased electrode capacitance, which could not be compensated completely with the pipette compensation setting on the Axopatch amplifier. However, this fixed capacitance can be compensated for with offline analysis [14]. This capacitance could introduce some small errors when calculating series resistance and membrane capacitance; it was neglected in our whole-cell experiments.

Mechanical Noise: There is up to 1 µm of total lateral movement of the pipette tip while in cell-attached configuration when the tungsten wire is advanced. This motion generally starts when the wire tip is less than 100 µm away from the pipette tip, resulting from the wire tip touching the pipette's inner wall and applying a lateral force. A single walled polyimide tubing as holder and protector tubes in order to make the rear end of the assembly more flexible and apply less lateral force on the inner walls of the pipette. A Pushpen electrode in which the tungsten wire tip is completely concentric with the pipette tip is desirable.

Chemical Noise: The introduction of the polyimide tubing does not introduce any chemical entity into the pipette solution, as it is inert [15]. The tungsten wire electrodes have been used to record extra/intracellular signals from cells. Applicants did not observe any difference in low pH sensitive A/M2 currents from CHO-K1 cells with or without the tungsten wire. However, were tungsten found to be toxic to specific cellular proteins, it could be replaced with another conical electrode (such as an etched platinum wire).

B. Operating the Pushpen Patch Clamp Electrode

The Pushpen operation requires installation of the tungsten wire (18) into the holder tube (42) and loading/unloading of the pipettes while avoiding damage to the wire. In order to install the tungsten wire, the hydraulic diaphragm (34) is advanced so that the holder tube protrudes from the protector tube. The tungsten wire is then snug fit into the holder tube and pulled back into the protector tube (38). Once the tungsten wire is inside the protector tube, a pipette (12) can be loaded onto the protector tube, avoiding any potential damage to the wire tip.

To ensure that no air bubbles are trapped inside the pipette solution, the loading of the pipette in the motorized pipette holder requires a two-step procedure. In the first step, after filling with electrolyte solution, the pipette is partially loaded onto the protector tube so that the tube's end barely touches the solution inside the pipette. The holder tube is then advanced until its tip is inside the solution, evacuating any air residing in the protector tube. The pipette is then fully loaded and the pipette cap, FIGS. 3a and 3c, tightened to air seal the pipette interior. The pipette tip can now be advanced towards a cell to permit patch clamping. Before removing a pipette, the wire must be retracted into the protector tube to avoid damaging its tip.

The tungsten wire is changed only when damaged, and the loading/unloading of the pipette takes just a few tens of seconds more than the same procedure with a conventional pipette holder.

C. Pushpen Operation to Obtain Whole-Cell Configuration

In a conventional patch-clamp experiment, a pulse of suction is applied in the cell-attached configuration to rupture the cell membrane and go whole-cell. During this procedure, a square pulse holding potential is applied to the membrane in the voltage clamp mode at regular intervals and the current is monitored. As soon as the membrane ruptures, one observes a rise in capacitive transients in the recorded current waveform due to the cell membrane capacitance. From the voltage and current waveforms, one can find the membrane capacitance, resistance, and series resistance [16]. In the Clampex software, the membrane test option in the cell mode, displays the current waveform and the membrane characteristics (FIG. 5a, 5b). Upon achieving whole cell configuration one can observe an increase in membrane capacitance and a decrease in series resistance. Applicants used the same methodology to detect the attainment of whole-cell configuration with the Pushpen operation.

Applicants carried out the following steps in order to obtain wholecell configuration with the Pushpen operation. The tungsten wire tip was brought to about 3 mm from the pipette tip, prior to advancing the pipette towards the cell membrane. Applicants have found that if the wire tip is too close to the pipette tip, suction on the cell membrane is insufficient to obtain a gigaseal. When the wire was advanced, the pipette interior was exposed to atmospheric pressure so that the displaced pipette solution can move up the pipette. The pipette was then advanced towards the cell until its tip touched the cell membrane. Gentle suction was then applied inside the pipette to obtain a gigaseal. The presence of mineral oil in the back chamber of the diaphragm (34) ensures that air is not sucked from the chamber side and enough negative pressure is applied on the cell membrane to achieve the gigaseal. After the formation of the gigaseal, the pipette interior was exposed to atmospheric pressure and the wire was continuously moved forward at a speed of 100 µm/sec until its tip was within 500 µm from the pipette tip. Perfusion of the bathing solution was then stopped while the wire was moved forward at a speed of 50 µm/sec until it is within 50 µm of the pipette tip. The motion controller was then switched to single step mode and pulses applied to move the wire forward at 200 nm/step. The membrane-test waveform in the Clampex software was observed at this time for changes in the capacitive transients while the wire moved forward. Once the wire impaled the cell membrane, a significant rise in capacitive transients was observed. FIGS. 5a, 5b are screen captures of Clampex and Motic Image Plus windows showing Whole-Cell Configuration obtained with the Pushpen operation using hydraulic actuator based motorized pipette holder. FIG. 5(a) shows cell-attached configuration where the tungsten wire has not yet impaled the cell membrane. A 200 nm step forward impales the cell membrane to obtain whole-cell configuration FIG. 5(b). Note the rise in capacitive transients and the change in membrane characteristics (upper-left corner in both images). Cm, Rm—membrane capacitance and resistance respectively, Ra is access (series) resistance. In FIG. 5(a) the capacitive transients are due to the uncompensated capacitance of the motorized pipette holder. The runtime calculations done by Clampex to calculate membrane capacitance, resistance, and series resistance showed an increase in capacitance and a decrease in series resistance from the values that were shown during the cell-attached configuration.

Mechanism of Going Whole-Cell with the Pushpen Operation:

Just as the mechanism for whole-cell generation conventionally is poorly understood, applicants can only hypothesize how whole-cell configuration is obtained with the Pushpen operation. Applicants believe that once the tungsten wire creates a hole in the cell membrane, this hole expands and the membrane flies towards the hydrophobic glass and away from the hydrophilic tungsten wire, although applicants do not wish or intend to be bound by any theory in this regard.

Pushpen Operation with Large Omega-Shape Membrane in the Pipette Tip:

In one instance, applicants observed an omega-shaped cell membrane with its end about 15 µm sucked into the pipette tip during formation of a gigaseal. In this case, whole-cell configuration was achieved when the wire tip was also about 15 µm from the pipette tip supporting the hypothesis that the cell membrane can be punctured with the wire.

Pushpen Operation Can Inflate Cells:

In an accidental scenario in the initial testing of the Pushpen operation, applicants observed that if the pipette interior is closed, the forward movement of the wire increases pressure on the pipette solution and pushes liquid into the cell to inflate it, later resulting in the disruption of the gigaseal. This procedure in a controlled manner might be used to deliver controlled quantities of liquids into cells.

Repeatability of the Pushpen Operation to Obtain Whole-Cell Configuration:

After establishing the technique and exploring the right parameters to perform the Pushpen operation, applicants successfully obtained whole-cell configuration with 10 individual cells. In this experience, obtaining wholecell configuration with the Pushpen operation is as repeatable as with the conventional method, but with a higher success rate.

Learning Curve of the Pushpen Operation:

The Pushpen system may have an advantage over the conventional patch-clamp approach to obtaining whole-cell configuration, particularly for novice electrophysiologists. Application of gentle suction to obtain a gigaseal is much easier than the application of a pulse of suction required to go whole-cell. It is common while trying to go whole-cell to apply excessive suction, resulting in movement of the pipette tip and disruption of the gigaseal. The Pushpen operation on the other hand offers a controlled way to obtain whole-cell configuration, as in general, position control is much easier than pressure control. The learning curve to obtain wholecell configuration with the Pushpen operation would therefore be much steeper than for the conventional method.

D. Low pH Activated A/M2 Currents Recorded after Obtaining Whole-cell Configuration with the Pushpen Operation To confirm the attainment of whole-cell configuration with the Pushpen operation, applicants measured whole-cell currents from CHO-K1 cells expressing Influenza A virus protein A/M2 (n=4) and compared the results with a previous study [20], where they recorded A/M2 currents with a conventional pipette holder (n=27). The A/M2 protein is a low pH activated ion channel, which conducts protons [19] and is inhibited by the drug amantadine [21]. Applicants obtained similar results for current records (amplitudes and time course) from CHO-K1 cells using the Pushpen operation and the conventional method to obtain whole-cell configuration.

Figure 6A:
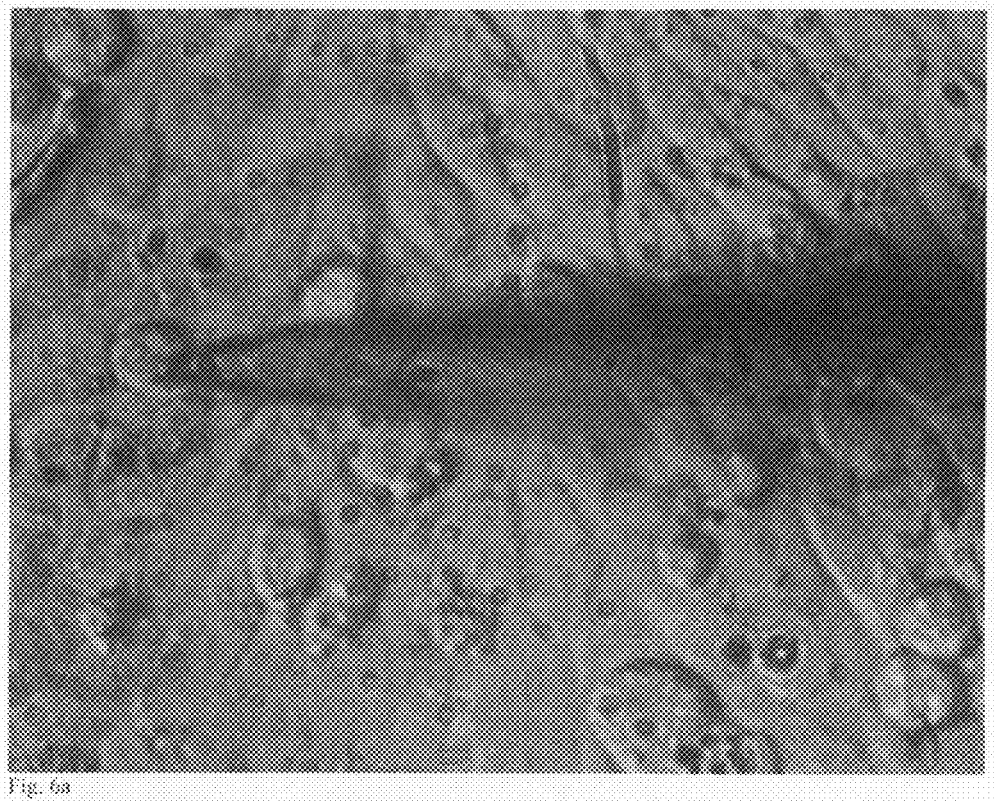
FIGS. 6a and 6b are optical microscope images of the cell-attached configuration (FIG. 6a) and push-pen operation to go whole-cell, (FIG. 6b).
Figure 6C:
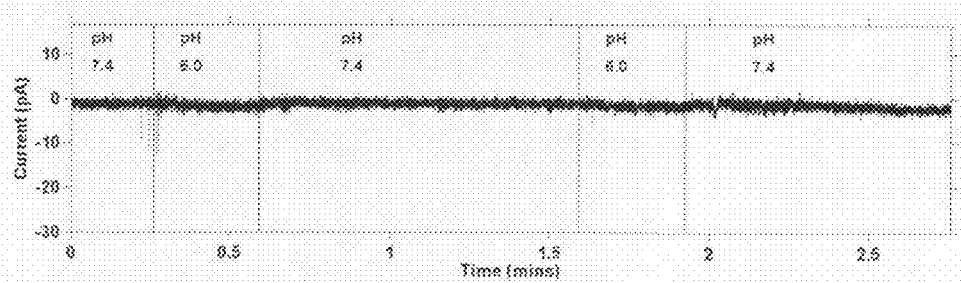
FIGS. 6c and 6d are electrical current records associated with the cell-attached operation and whole-cell operation, respectively, measured from CHO-K1 cells expressing influenza A virus protein A/M2, which is a low pH sensitive ion channel that conducts protons into the cell (negative current). The drug amantadine is used to block A/M2 currents. In the FIG. 6c trace, cell-attached configuration (wire position of FIG. 6a), low pH activated currents are not observable. In the FIG. 6d trace after going whole-cell with push-pen operation (wire position of FIG. 6b), amantadine inhibited currents are visible indicating A/M2.
Figure 6B:
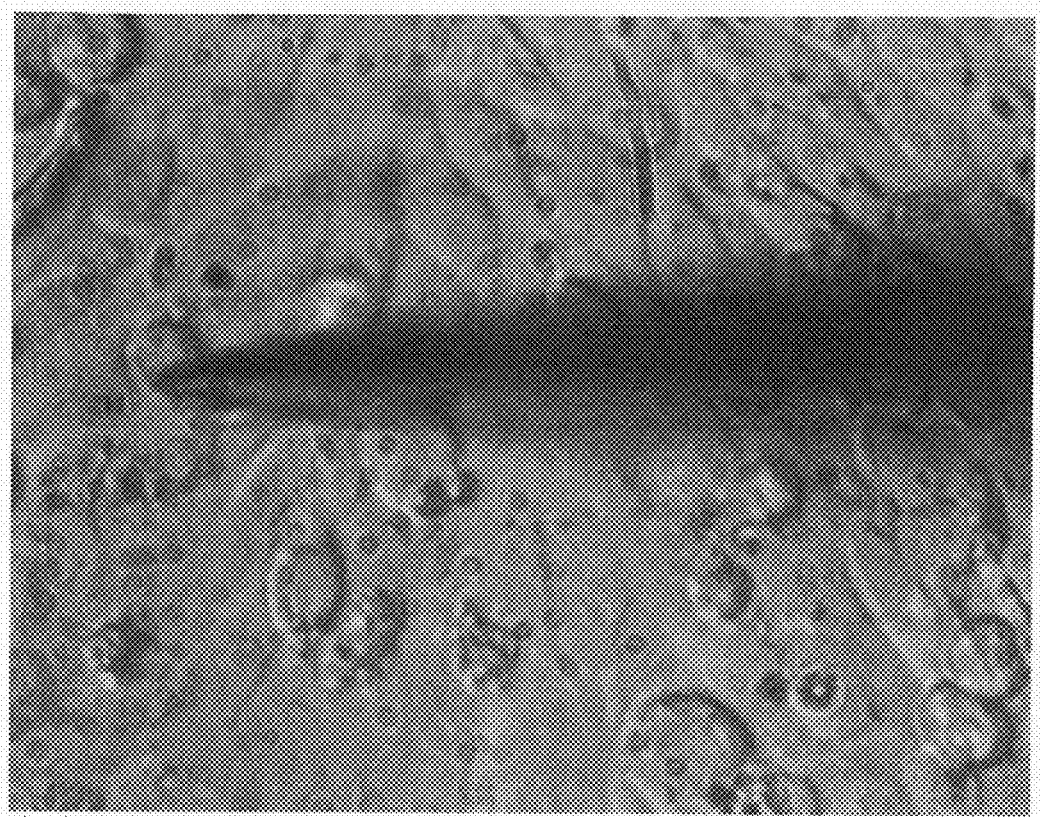
Figure 6D:
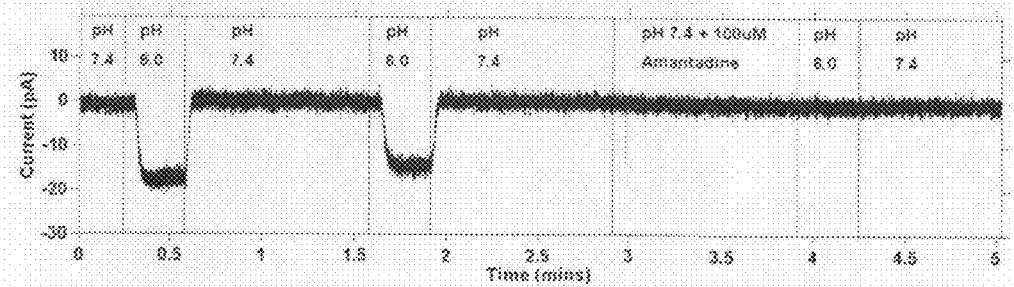

The A/M2 whole-cell currents from CHO-K1 cells were also similar to those obtained in other mammalian cells [22], FIG. 6c, 6d show representative A/M2 current records obtained in cell-attached and whole-cell configurations (obtained with Pushpen operation) along with the respective images.

In the cell-attached configuration (FIG. 6a), the tungsten wire is located at a distance of about 20 μm from the pipette tip. The application of activating solution (pH 6.0) here did not induce any membrane currents (current trace of FIG. 6c). Two applications of the activating solution were tested with a gap of 1 min washout with non-activating solution (pH 7.4). Later, the perfusion was stopped and the wire advanced to obtain whole-cell configuration as explained in the previous section.

The cell-attached and whole-cell configurations are shown in FIGS. 6a and 6b, respectively, along with respective cell-attached and whole-cell current records and (FIGS. 6c and 6d) measured from CHO-K1 cells expressing influenza A virus protein A/M2. A/M2 is a low pH sensitive ion channel that conducts protons. Extracellular application of low pH solution results in channel opening and movement of protons into the cell (negative current). The drug amantadine is used to block A/M2 currents. In the FIG. 6c current trace, cell-attached configuration, low pH activated currents are not observable. In the FIG. 6d trace after going whole-cell with Pushpen operation, amantadine inhibited currents are visible indicating A/M2 activity.

In the whole-cell configuration (FIG. 6b), the tungsten wire has already impaled the cell membrane. The application of activating solution here induces pH sensitive proton currents (FIG. 6d). Two applications of activating solution with a gap of 1 min washout with non-activating solution gave similar results to the current trace. After a further washout for 1 min with non-activating solution, non-activating solution containing 100 μm amantadine was applied for 1 min to inhibit the A/M2 ion channel [19], [21]. Later the application of activating solution did not induce any membrane current confirming that applicants recorded A/M2 membrane currents with the previous applications of the activating solution.

Perfusion does not Disrupt the Gigaseal in Whole-Cell Configuration Obtained with Pushpen Operation:

In these experiments, the solutions were introduced at a distance of about 1 mm from the patched cells. As can be seen from the current trace in FIG. 6d, the perfusion does not disrupt the gigaseal of the whole-cell configuration achieved with the Pushpen operation.

Comparison of Pushpen Operation with Conventional Method to Obtain Whole-Cell Configuration in CHO-K1 Cells Expressing A/M2:

Since A/M2 has a basal activity around physiological pH (7.0-7.5), it causes intracellular pH fluctuations, which are unhealthy for mammalian cells [25], [22]. Therefore, cells expressing A/M2 are difficult to patch onto and to establish and maintain in whole-cell configuration. In a previous study [20] with a conventional patch clamp electrode, applicants spent an average of 9.3 hours per cell to obtain stable whole-cell current recordings. With the Pushpen operation pursuant to the invention, the success rate for maintaining whole-cell current recordings with this difficult preparation improved markedly (same experimenter) to 5 hours per cell. Although this result is anecdotal, it encourages belief that the Pushpen operation increases the yield in our whole-cell recordings with CHO-K1 cells expressing A/M2. The Pushpen operation may be used to obtain whole-cell configuration with other cell types.

The present invention thus provides a patch-clamp electrode based on Pushpen operation, where a conical electrode moves linearly inside the pipette and can protrude from the pipette tip like a push pen. The present invention provides a novel way to obtain whole-cell configuration from cell-attached mode by impaling the cell membrane with a tungsten or other wire without disrupting the gigaseal and without need of a pulse of suction (as in the conventional patch-clamp method). Practice of the invention to obtain whole-cell configuration is easier to learn and can lead to automation of this procedure.

Pushpen operation may reduce series resistance as depicted in the results of a separate modeling study [23] and improve recording bandwidth. Additionally, Pushpen operation may effectively, clear clogged pipette tips and lead to the prolongation of recording sessions, and may prevent cytosol diffusion into the pipette, thus maintaining control over cellular integrity.

Although the invention has been described in connection with certain embodiments, those skilled in the art will appreciate that changes and modifications can be made therein within the scope of the invention as set forth in the appended claims.

REFERENCES

[1] E. Neher and B. Sakmann, "Single-channel currents recorded from membrane of denervated frog muscle fibres". Nature, vol. 260, pp. 799802, April 1976.

[2] O. P. Hamill, A. Marty, E. Neher, B. Sakmann, and F. J. Sigworth, "Improved Patch Clamp Technique for high-resolution current recording from cells and cell-free membrane patches", Pflugers Archive European J. of Physiology, vol. 391, pp. 85-100, August 1981.

[3] H. Sontheimer, and M. L. Olsen, "Whole-Cell Patch Clamp Recordings", Patch-Clamp Analysis: Advanced Techniques, 2nd Ed. Neuromethods, 38, pp. 35-68, 2007.

[4] "Instrumentation for measuring Bioelectric signals from cells", The Axon Guide, 2nd Edition, Molecular Devices, USA. pp. 59

[5] A. J. Sherman, A. Shrier, and E. Cooper, "Series resistance compensation for whole-cell patch-clamp studies using a membrane state estimator", Biophysical J., vol. 77, pp. 2590-2601, November 1999.

[6] S. F. Traynelis, "Software-based correction of single compartment series resistance errors", J. of Neuroscience Methods, vol. 86, pp. 25-34. 1998.

[7] F. Bezanilla and E. Stefani, "Gating Currents", Methods in Enzymology, vol. 293, pp 331-352, 1998.

[8] J. T. Davie, M. H. P. Kole, I. J. Letzkus, E. A. Rancz, N. Spruston, G. I. Stuart, and M. Hausser, "Dendritic patch clamp recording". Nature Protocols, vol. I, no. 3 pp. 1235-1247, November 2006.

[9] A. Marty, and J. Zimmerberg, "Diffusion into the patch-clamp recording pipette of a factor necessary for muscarinic current response", Cell Signal, vol. I, no. 3, pp. 259-268, 1989.

[10] W. Walz, "Perforated Patch-Clamp Technique", Patch-Clamp Applications and Protocols, Neuromethods, 26, 155-171, 1995.

[11] Y. Zhao, S. Inayat, D. A. Dikin, J. H. Singer, R. S. Ruoff, and J. B. Troy, "Patch clamp technique: review of the current state of the art and potential contributions from nanoengineering", J. Of Nanoengineering and Nanosystenis, vol. 222, pp. I-11, 2009.

[12] G. Miesenbock, D. A. De-Angelis, and J. E. Rothman, J, E, "Visualizing secretion and synaptic transmission with pH-sensitive green fluorescent proteins," Nature, vol. 394 (6689), pp. 192-195, 1998.

[13] G. Dernick, "Simultaneous detection of Fusion and secretion by patch amperometry of exocytosis of small vesicles", PhD Dissertation, Carola University of Heidelberg, Germany, 1999

[14] H. Nadeau, and H. A. Lester, "Two-compartment model for whole-cell data analysis and transient compensation", Journal of Neuroscience Methods, vol. 99, pp. 25-35, March 2000.

[15] X. M. Shao, and J. L. Feldman, "Micro-agar salt bridge in patch-clamp electrode holder stabilizes electrode potentials". Journal of Neuroscience Methods, vol. 159, pp. 108-115, July 2007.

[16] pClamp 10, "Data Acquisition and Analysis for Comprehensive Electrophysiology, User Guide, Molecular Devices, USA, pp 163-166

[17] M. Sokabe, and F. Sachs, "The structure and dynamics of patchclamped membranes: a study of differential interference microscopy", J. Of Cell Biology, vol. I 11, pp. 599-606, 1990.

[18] T. M. Suchyna, V. S. Markin, and F. Sachs, 'Biophysics and Structure of the Patch and the Gigaseal", Biophysical J., vol. 97, pp. 738-747, August 2009.

[19] L. H. Pinto, L. J. Holsinger, and R. A. Lamb, "Influenza virus M2 protein has ion channel activity", Cell, vol. 69, pp. 517-528, 1992.

[20] V. Balannik, P. Obrdlik, S. Inayat, C. Steensen, J. Wang, I. M. Rausch. W. F. DeGrado, B. Kelety, and L. H. Pinto, "Solid supported membrane technology for the investigation of the influenza A virus M2 Channel Activity", Pflugers Archive European J. of Physiology. vol. 459 (4), pp. 593-605, November 2009.

[21] C. Wang, K. Takeuchi, L. H. Pinto and R. A. Lamb. "Ion channel activity of influenza A virus M2 protein: characterization of the amantadine block", JJ of F'irology, vol. 67, pp. 5585-5594

[22] I. V. Chizhmakov, F. M. Geraghty, D. C. Ogden. A. Hayhurst, M. Antoniou, and A. J. Hay, "Selective proton permeability and pH regulation of the influenza virus M2 channel expressed in mouse erythroleukaemia cells", J. of Physiology-, vol. 494 (2). pp. 329-336. July 1996.

[23] Y. Zhao, S. lnayat, D. A. Dikin, R. S. Ruoff, and J. B. Troy. "'Impedance characterization and modelling of an improved patch clamp device". J. Of Nanoengineering and Nanosystems, in press. February 2010.

[24] I. V. Chizhmakov, D. C. 0-den, F. M. Geraghty, A. Hayhurst, A. Skinner, T. Betakova, and A. J. Hay, "Differences in conductance of M2 proton channels of two influenza viruses at low and high pH", JJ of Physiolop. vol. 546 (2). pp. 427-438, January 2003.

[25] K. Giffin, R. K. Rader, M. H. Marino. and R. W. Forgey, "Novel assay for the influenza virus M2 channel activity", Federation Of European Biochemical Socities. Letters, vol. 357, pp. 269-274, 1995.

[26] G. Dernick, L-W. Gong, L. Tabares, G. A. de Toledo, and M. Lindau, "Patch amperometry: high-resolution measurements of single-vesicle fusion and release", Nature Methods, vol. 2(9), pp. 699-708, September 2005.

The invention claimed is:

1. An electrode comprising a pipette having an open tip, a transducer on a carrier assembly disposed for movement in the pipette, and an actuator configured to move the carrier assembly in the pipette, wherein the carrier assembly comprises an inner protrudable member movable in the pipette by the actuator and on which protrudable member the transducer comprising a silver wire coated with AgCl is wound and insulated by an insulating tube disposed around the protrudable member therebetween, wherein the transducer on the insulating tube moves with the inner protrudable member in the pipette, and wherein the inner protrudable member has a pointed end movable past and outside the pipette open tip to a controlled testing position.

2. The electrode of claim 1 wherein the transducer comprises a single silver wire coated with AgCl and wherein the protrudable member has a pointed end movable past and outside of the pipette open tip to the controlled testing position.

3. The electrode of claim 2 wherein the protrudable member has a pointed wire end that is movable past and outside the pipette open tip to the controlled testing position.

4. The electrode of claim 1 wherein the protrudable member comprises a pointed end rod or pointed end tube.

5. The electrode of claim 1 wherein the protrudable member is a voltage-transducing metallic member.

6. The electrode of claim 1 wherein the actuator comprises an electrical actuator or other linear actuator.

7. The electrode of claim 1 wherein the actuator comprises a hydraulic actuator.

* * * * *